Figure 1:
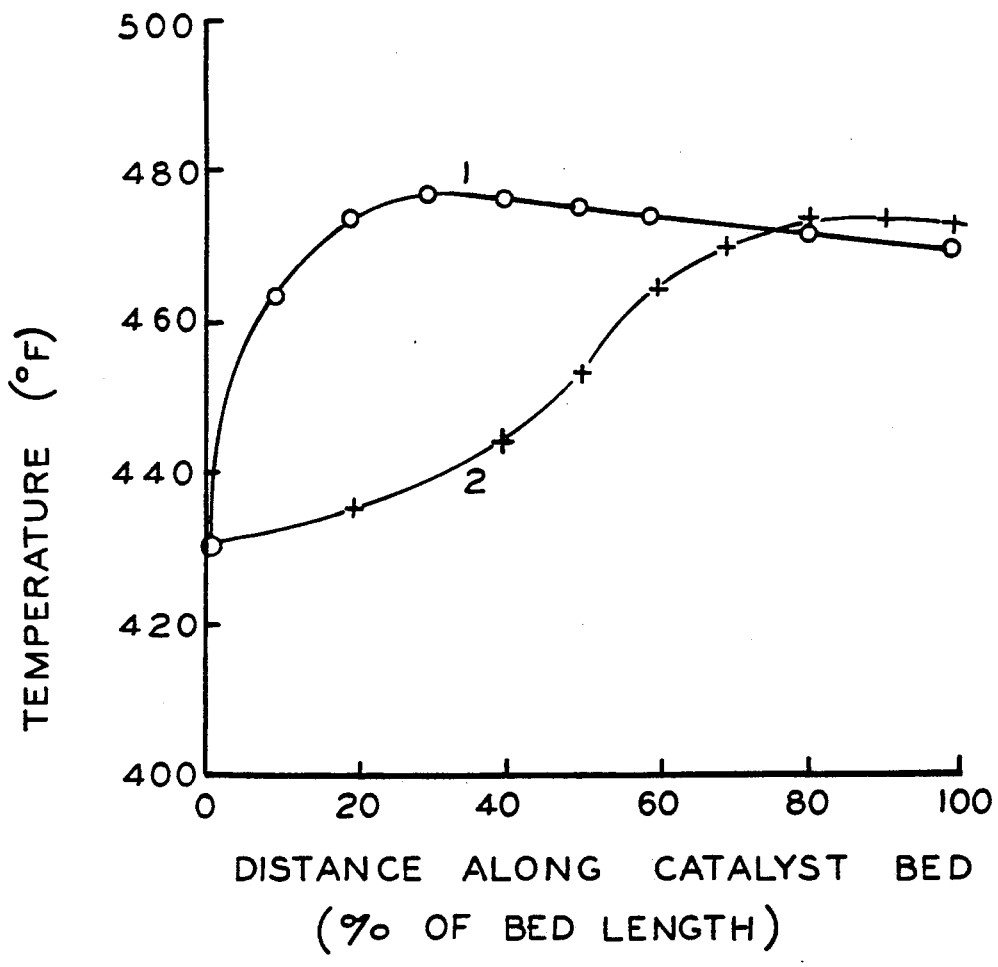

United States Patent [19]

Khonsari et al.

[11] Patent Number: 5,118,897
[45] Date of Patent: Jun. 2, 1992

[54] REACTIVATION OF ALKYLATION CATALYSTS

[75] Inventors: Ali M. Khonsari, Bloomfield; George D. Suciu, Ridgewood, both of N.J.

[73] Assignee: ABB Lummus Crest Inc., Bloomfield, N.J.

[21] Appl. No.: 778,481

[22] Filed: Oct. 17, 1991

Related U.S. Application Data

[63] Continuation-in-part of Ser. No. 584,378, Sep. 17, 1990, abandoned, which is a continuation of Ser. No. 460,669, Dec. 12, 1989, abandoned, which is a continuation of Ser. No. 330,741, Mar. 30, 1989, abandoned.

[51] Int. Cl.$^5$ ............................................. C07C 2/68
[52] U.S. Cl. .................................................. 585/467
[58] Field of Search .......................................... 585/467

[56] References Cited

U.S. PATENT DOCUMENTS

| | | | |
|---|---|---|---|
| 3,389,077 | 6/1968 | Glein et al. | 502/30 |
| 3,851,004 | 11/1974 | Yang | 502/30 |
| 4,008,291 | 2/1977 | Zabransky et al. | 502/30 |
| 4,049,739 | 9/1977 | Zabransky et al. | 502/30 |
| 4,626,609 | 12/1986 | Shihabi | 585/467 |
| 4,658,075 | 4/1987 | Dessau et al. | 585/467 |
| 4,876,408 | 10/1989 | Ratcliffe et al. | 585/467 |
| 4,973,780 | 11/1990 | Johnson et al. | 585/467 |

FOREIGN PATENT DOCUMENTS 0070840  6/1981  Japan.

Primary Examiner—Patrick P. Garvin
Assistant Examiner—E. D. Irzinski
Attorney, Agent, or Firm—Elliot M. Olstein; Raymond J. Lillie

[57] ABSTRACT

A process for reactivating alkylation catalyst which comprises contacting alkylation catalyst with hydrogen and benzene in the essential absence of olefin. The reactivation process may be conducted under conditions (eg., temperature, pressure) similar to that employed in an alkylation reaction. This process enables one to reactivate the catalyst in situ in a relatively short time, thus minimizing disruption of the alkylation operation.

6 Claims, 1 Drawing Sheet

REACTOR TEMPERATURE PROFILE

REACTOR TEMPERATURE PROFILE

REACTIVATION OF ALKYLATION CATALYSTS

This application is a continuation-in-part of application Ser. No. 584,378, filed Sep. 17, 1990, which is a continuation of application Ser. No. 460,669, filed Dec. 12, 1989, now abandoned, which is a continuation of application Ser. No. 330,741 filed Mar. 30, 1989, now abandoned.

This invention relates to the reactivation of an alkylation catalyst. More particularly, this invention relates to the reactivation of an alkylation catalyst in situ, and under conditions similar to those employed for conducting alkylation reactions.

In an alkylation reaction, benzene and an olefin (for example, ethylene, propylene, or butylene) are reacted in an alkylation reactor, under catalytic conversion conditions, in the presence of an alkylation catalyst, to produce alkylbenzene (for example, ethylbenzene, cumene, or other alkylbenzenes, depending upon the olefin employed). The alkylation reactor contains one or more beds of alkylation catalyst. The catalyst may be a zeolite catalyst or other type of acidic catalyst.

The alkylation reaction may be carried out in the liquid phase, in the vapor phase, or in a mixed gas-liquid phase. As increasing amounts of raw materials (benzene and olefin) are passed over the catalyst bed, the activity of the catalyst decreases gradually. The rate at which catalyst activity decreases depends upon the properties of the catalyst used, the olefin used, and the benzene to olefin molar ratio. The rate of deactivation of the catalyst also depends upon operating conditions such as feed rates of the benzene and olefin, the space velocity, as well as the reaction temperature and pressure conditions.

For example, when benzene is alkylated with ethylene in the vapor phase to produce ethylbenzene in the presence of a zeolite catalyst, deactivation of the catalyst makes it necessary to regenerate the catalyst after every 20 to 40 days of catalyst operation. When benzene is alkylated with ethylene in the liquid phase or a mixed vapor-liquid phase, the time interval between regenerations may be 12 months or longer.

Regeneration of the catalyst may be carried out either within the reactor itself (in situ) or outside the reactor (ex situ). In both cases, the reactor must be taken off stream, and all organics contained within the reactor must be removed (eg., by stripping with an inert gas, steam, etc.), and the regeneration is conducted by a controlled combustion of the polymeric or other carbonaceous compounds which have accumulated on the surface or within the pores of the catalyst. In order to prevent structural degradation of zeolitic catalysts or permanent loss of activity, temperatures during the combustion process should not increase or decrease rapidly, and the maximum regeneration temperature should not exceed 625° C. After the organic material has been combusted, the catalyst may be flushed with an inert gas, cooled, and then re-used in an alkylation reaction. If the regeneration were performed in an off-site reaction zone, the catalyst must be re-introduced into the reactor. The regeneration process hereinabove described is lengthy and often leads to lost production.

In accordance with an aspect of the present invention, there is provided a process for reactivating an alkylation catalyst. The process comprises contacting alkylation catalyst with hydrogen and benzene in the essential absence of olefin. In a preferred embodiment, the reactivation process may be carried out under temperature and pressure conditions which are similar to conditions employed in an alkylation reaction. The reactivation may be carried out at a temperature of from about 350° F. to about 800° F., preferably from about 425° F. to about 525° F., and at a pressure of about 300 psig to about 3,000 psig, preferably from about 350 psig to about 550 psig. The flow rate of benzene may be at a WHSV (weight hourly space velocity) of from about 0.1 to 10.0 preferably from about 1.0 to about 5.0. The flow rate of hydrogen may be at a VHSV (volume hourly space velocity) of from about 2 to about 100 $Hr.^{-1}$, preferably from about 10 to about 50 $Hr.^{-1}$. The reactivation process may take place for a period of time of from about 1 hour to about 50 hours, preferably from about 5 hours to about 20 hours.

The catalysts to which this reactivation procedure can be applied are those used in heterogeneous alkylation or transalkylation reactions, especially zeolites in acidic form, such as zeolite X, zeolite Y, zeolite L, zeolite Beta, ZSM-5, Omega crystal zeolites, mordenite, and chabazite.

In accordance with another aspect of the present invention, there is provided a process for producing alkylbenzene which comprises contacting olefin and benzene with an alkylation catalyst to produce alkylbenzene, and reactivating the alkylation catalyst with benzene and hydrogen in the essential absence of olefin. The reactivation of the alkylation catalyst preferably may be carried out under conditions as hereinabove described, and the catalyst preferably is a zeolite catalyst.

The reactivation process in accordance with the present invention may be implemented by stopping the flow of olefin to an alkylation reactor when one desires to reactivate the catalyst. The flow of benzene to the reactor is allowed to continue. A stream of hydrogen gas is then also fed to the reactor, either as a separate stream, or the hydrogen is admixed with the benzene, and then fed to the reactor. The flow rate of the benzene may be from 0.01 to 1.0 times the flow rate during the alkylation period, preferably from 0.2 to 0.5 times the flow rate.

Although the present invention is not to be limited to any theoretical reasoning, it has been postulated that, during the alkylation of benzene with olefin in the reactor, parallel reactions such as dimerization and polymerization of the olefin, and dehydrogenations of alkylated products, isomerizations, and other polymerizations occur. These parallel reactions, however, may produce materials with high molecular weights which are strongly adsorbed on active sites of the catalyst, thus resulting in deactivation of the catalyst. Benzene, whether passed over the catalyst bed at high or low temperatures is unable to reactivate the catalyst. The materials deposited upon the catalyst appear to have a strong chemisorption and/or extremely low solubility in benzene. When hydrogen, however, is fed to the reactor along with benzene, the hydrogen appears to be able to penetrate the layer of adsorbed materials, and cause the physical desorption of these materials or involve the materials in reactions at the active sites (eg., isomerizations, hydrogenolyses) by which the adsorbed molecules are fragmented and/or the polarity of the molecules is destroyed. The molecules thus desorb from the catalyst surface and are washed away by the flowing benzene.

The invention will now be described with respect to the drawing, wherein

The drawing is a graph of temperature profiles of active and deactivated catalyst wherein a plot of temperature vs. distance along catalyst bed is developed.

The invention will now be described with respect to the following examples; however, the scope of the present invention is not intended to be limited thereby.

EXAMPLE 1

Operation with active catalyst.

The experimental apparatus consists of a fixed bed reactor provided with efficient thermal insulation in order to minimize heat losses and to operate in adiabatic conditions. The reactor is provided with an axially-located traveling thermocouple. Through the bottom end, a stream of benzene (B) and ethylene (E) are fed. The two reagents are metered separately, mixed and preheated before entering the reactor. The reactor effluent is cooled and analyzed. The operating conditions (temperature, pressure, molar B/E ratio, space velocity) are selected so as to achieve the complete conversion of the ethylene. The profile of temperature vs. distance along catalyst bed (% of bed length) was plotted on the graph as Curve 1. Since the alkylation is exothermic, at steady state, a characteristic temperature profile is established in the catalyst bed. Essentially all the limiting reagent (ethylene) has reacted at the bed depth at which the maximum value of the temperature occurs.

The temperature profile plotted as Curve 1 on the graph was obtained in the following operating conditions:

| | |
|---|---|
| Benzene feed rate (g/g catalyst × hr.): | 10 |
| B/E (mol/mol) | 12 |
| Preheat temperature (°F.) | 423 |
| Pressure (psig) | 400 |

EXAMPLE 2

Operation with deactivated catalyst.

The same experimental apparatus as described in Example 1 was used. After a prolonged operation period, the temperature profile was plotted and is depicted by Curve 2 of the graph. The operating conditions are identical to those of Example 1. Due to the partial deactivation of the catalyst, the reaction rate is lowered and therefore the temperature increase is slower than that in Example 1.

EXAMPLE 3

Catalyst Reactivation

The experimental apparatus described in Example 1 was used. In order to reactivate the catalyst, the flow of ethylene was interrupted and a stream of $H_2$ gas was introduced in the reactor, together with the benzene. The following conditions were used:

| | |
|---|---|
| Temperature (°F.) | 450 |
| Pressure (psig) | 400 |
| Flow rate of benzene (g/g cat × hr.) | 8 |
| Flow rate of $H_2$ (g/g cat bed × hr.) | 0.006 |
| Duration of treatment (hr.) | 10 |

Upon completion of the treatment, the flow of $H_2$ was stopped, and the operating conditions reported in Example 1 were reestablished. After the steady state was achieved, the temperature profile along the bed was measured and was found to be identical to that plotted as Curve 1 in the graph. This indicates that the catalyst has fully recovered its alkylation activity.

EXAMPLE 4

The reactivation was attempted without the use of hydrogen. A deactivated catalyst bed showing a temperature profile similar to that given by Curve 2 of the graph was treated in the conditions described in Example 3 with the difference that no flow of the $H_2$ gas was used. After 10 hours under these conditions, the operating parameters given in Example 1 were reestablished. Upon reaching steady-state, the temperature profile along the bed was measured. The curve recorded was identical to that measured before the treatment (Curve 2). This indicates that no reactivation of the catalytic activity was achieved.

Advantages of the present invention include the ability to reactivate the alkylation catalyst in situ under conditions similar to those employed for the alkylation reaction. In addition, the reactivation may be accomplished in a relatively short time, resulting is a minimal disruption of the alkylation operation. With the exception of H2, no additional chemicals are used in the reactivation, and no waste materials which require separate treatment are produced. The effluent from the reactor resulting from the reactivation process may be processed in the same equipment as the effluent produced as a result of an alkylation reaction.

It is to be understood, however, that the scope of the present invention is not to be limited to the specific embodiments described above. The invention may be practiced other than as particularly described and still be within the scope of the accompanying claims.

What is claimed is:

1. A process for producing alkylbenzene, comprising: contacting olefin and benzene with a catalyst consisting essentially of a zeolite alkylation catalyst to produce alkylbenzene; and
reactivating said zeolite alkylation catalyst by contacting said zeolite alkylation catalyst with benzene and hydrogen in the essential absence of olefin.

2. The process of claim 1 wherein said alkylation catalyst is contacted with benzene and hydrogen at a temperature of from 350° F. to about 800° F.

3. The process of claim 2 wherein said alkylation catalyst is contacted with benzene and hydrogen at a temperature of from about 425° F. to about 525° F.

4. The process of claim 1 wherein said alkylation catalyst is contacted with benzene and hydrogen at a pressure of from about 300 psig to about 3,000 psig.

5. The process of claim 4 wherein said alkylation catalyst is contacted with benzene and hydrogen at a pressure of from about 350 psig to about 550 psig.

6. The process of claim 1 wherein said zeolite alkylation catalyst is selected from the group consisting of zeolite X, zeolite Y, zeolite L, zeolite Beta, ZSM-5, Omega crystal zeolites, mordenite, and chabazite.

* * * * *